United States Patent [19]

Schwindeman

[11] Patent Number: 5,321,148
[45] Date of Patent: Jun. 14, 1994

[54] PROCESS FOR PREPARING FUNCTIONALIZED ALKYLLITHIUM COMPOUNDS

[75] Inventor: James A. Schwindeman, Charlotte, N.C.

[73] Assignee: FMC Corporation, Philadelphia, Pa.

[21] Appl. No.: 175,833

[22] Filed: Dec. 30, 1993

[51] Int. Cl.$^5$ .............................. C07F 7/08; C07F 7/18
[52] U.S. Cl. .................................. 556/466; 556/482; 556/486
[58] Field of Search ............... 556/466, 482, 486

[56] References Cited

U.S. PATENT DOCUMENTS

| | | | |
|---|---|---|---|
| 3,511,865 | 5/1970 | Peterson | 556/460 |
| 5,082,961 | 1/1992 | Fukumoto et al. | 556/466 |
| 5,231,205 | 7/1993 | Rieke | 556/466 X |

Primary Examiner—Paul F. Shaver
Attorney, Agent, or Firm—Robert L. Andersen; Charles C. Fellows

[57] ABSTRACT

A process for preparing functionalized alkyllithium compounds comprising reacting a fine particle size lithium metal of not more than 300 microns average particle size with an organosiloxyalkyl halide of the formula $R^1R^2R^3SiORX$ wherein $R^1$, $R^2$ and $R^3$ are independently selected from alkyl groups containing 1 to 10 carbon atoms and aryl groups containing 6 to 10 carbon atoms, R is selected from alkyl groups containing 1 to 8 carbon atoms either straight chain or substituted by alkyl or aryl groups, X is selected from chlorine or bromine, the reaction temperature is above 50° C., the reaction medium is a hydrocarbon solvent and the reaction is conducted in an inert atmosphere.

6-(t-butyldimethylsilyloxy)-1-hexylhalide, 3-(t-butyldimethyl-silyloxy)-2,2-dimethyl-1-propylhalide, 3-(t-butyldimethylsilyloxy)-1-propylhalide, 4-(t-butyldimethylsilyloxy)-1-butylhalide, 3-(t-butyldimethyl-silyloxy)-2-methyl-1-propylhalide 8-(t-butyldimethylsilyloxy)-1-octylhalide, 6-(triisopropylsilyloxy)-1-hexylhalide, 3-(triisopropylsilyloxy)-2,2-dimethyl-1-propylhalide; 3-(triisopropylsilyloxy)-1-propylhalide, 4-(triisopropylsilyloxy)-1-butylhalide, 3-(triisopropylsilyloxy)-2-methyl-1-propylhalide, 8-(triisopropylsilyloxy)-1-octylhalide, 6-(t-butyldiphenylsilyloxy)-1-hexylhalide, 3-(t-butyldiphenylsilyloxy)-2,2-dimethyl-1-propylhalide, 3-(t-butyldiphenylsilyloxy)-1-propylhalide, 4-(t-butyldiphenylsilyloxy)-1-butylhalide, 3-(t-butyldiphenylsilyloxy)-2-methyl-1-propylhalide and 8-(t-butyldiphenylsilyloxy)-1-octylhalide.

13 Claims, No Drawings

PROCESS FOR PREPARING FUNCTIONALIZED ALKYLLITHIUM COMPOUNDS

The present invention concerns an improved process for preparing functionalized alkyllithium compounds of the formula $R^1R^2R^3SiORLi$.

Functionalized organolithium compounds have been used in organic synthesis reactions for some time and more recently have been used as initiators in an anionic polymerization of olefinic monomers. United Kingdom published patent application 2,241,239 discloses producing initiators of the formula $R^1R^2R^3SiOALi$ wherein $R^1$, $R^2$ and $R^3$ are aliphatic and aromatic radicals and A is a hydrocarbon bridging group. This patent recommended using a 1.5 to 6 stoichiometric excess of lithium, an excess of 6 was used in the examples, to get high yields. Reaction temperatures below 50° C. were employed because above 40° C. undesired by-products were observed.

The present invention provides a process for preparing functionalized alkyllithium compounds by reacting a fine particle size lithium metal of not more than 300 microns average particle size with an organosiloxyalkyl halide of the formula $R^1R^2R^3SiORX$ wherein $R^1$, $R^2$ and $R^3$ are independently selected from alkyl groups containing 1 to 10 carbon atoms and aryl groups containing 6 to 10 carbon atoms, R is selected from alkyl groups containing 2 to 8 carbon atoms either straight chain or substituted by alkyl or aryl groups, X is selected from chlorine or bromine, the reaction temperature is above 50° C., the reaction medium is a hydrocarbon solvent and the reaction is conducted in an inert atmosphere.

The compounds of the formula $R^1R^2R^3SiORX$ are prepared in hydrocarbon solution from the corresponding haloalcohol, HORX, wherein R and X have the meanings ascribed above, which is reacted with a triorganosilylhalide of the formula $R^1R^2R^3SiX$ where in $R^1$, $R^2$ and $R^3$ have the meanings ascribed above and X may be the same or different halogen but preferably is chlorine.

Triorganosilyloxy halides useful in the practice of this invention include, but are not limited to those containing a t-butyldimethylsilyl, trimethylsilyl or dimethylphenylsilyl group and the like, which includes but is not limited 6-(t-butyldimethylsilyloxy)-1-hexylhalide, 3-(t-butyldimethylsilyloxy)-2,2-dimethyl-1-propylhalide, 3-(t-butyldimethylsilyloxy)-1-propylhalide, 4-(t-butyldimethylsilyloxy)-1-butylhalide, 3-(t-butyldimethylsilyloxy)-2-methyl-1-propylhalide 8-(t-butyldimethylsilyloxy)-1-octylhalide, 6-(triisopropylsilyloxy)-1-hexylhalide, 3-(triisopropylsilyloxy)-2,2-dimethyl-1-propylhalide; 3-(triisopropylsilyloxy)-1-propylhalide, 4-(triisopropylsilyloxy)-1-butylhalide, 3-(triisopropylsilyloxy)-2-methyl-1-propylhalide, 8-(triisopropylsilyloxy)-1-octylhalide, 6-(t-butyldiphenylsilyloxy)-1-hexylhalide, 3-(t-butyldiphenylsilyloxy)-2,2-dimethyl-1-propylhalide, 3-(t-butyldiphenylsilyloxy)-1-propylhalide, 4-(t-butyldiphenylsilyloxy)-1-butylhalide, 3-(t-butyldiphenylsilyloxy)-2-methyl-1-propylhalide 8-(t-butyldiphenylsilyloxy)-1-octylhalide and the like.

The reaction solvent is a non-polar hydrocarbon solvent selected from aliphatic, cycloaliphatic and aromatic hydrocarbons or mixtures thereof. Preferred solvents are aliphatic, cycloaliphatic and aromatic hydrocarbons, especially alkanes having 3 to 12 carbon atoms, cycloalkanes having 4 to 8 carbon atoms and aromatic hydrocarbons having 6 to 8 carbon atoms and mixtures thereof.

The lithium metal is used in particulate form of not greater than 300 micron average particle size and preferably 10 to 300 microns. The lithium typically contains 0.4 to 0.76 weight percent sodium and is used in amounts in excess of stoichiometric of 1 to 100% preferably 20- to 40% excess. The lithium dispersion is prepared for use by washing several times with pentane or some other hydrocarbon solvent of choice, to remove the dispersing fluid, and preferably subjected to high speed agitation at elevated temperatures to condition the lithium for the reaction.

The reaction temperature is from at least 50° C. up to just below the decomposition temperature of the product, and preferably from 50° C. up to the boiling point of the solvent with reflux temperatures being most preferred. The optimal temperature for running the reaction can be exceeded by using only a high boiling solvent such as decane (BP-174° C.). See 8602 and 8603 in the table which show a lower yield when high boiling solvent is employed. The useful temperature range for operating the process is between about 50° C. and about 160° C. Reduced or elevated temperature can be employed if desired but are not required. The reactants and the products are not involve highly corrosive so many materials of construction can be used for the reactor and related process equipment.

According to the process of the present invention, the lithium metal dispersion, when prepared in mineral oil, was washed free of mineral oil with a hydrocarbon solvent, dried in a stream of argon and transferred to the reaction vessel with the hydrocarbon solvent. The mixture of clean metal and hydrocarbon was heated to the reaction temperature and the functionalized triorganosiloxyalkyl halide of the formula $R^1R^2R^3SiORX$ was added slowly to the heated lithium metal-hydrocarbon solvent mixture. The reaction was controlled by cooling the reaction mixture. An exotherm developed after 10-15% of the halide was added. At the end of the halide feed, the reaction temperature rapidly declined to room temperature. The reaction mixture was stirred several hours at room temperature, then transferred to a sintered glass filter. The solution filtered rapidly with 3 psi ($20.68 \times 10^3$ Pa) Argon pressure. The resultant non-turbid solution was analyzed for total base, active carbon-lithium (modified Watson-Estham titration) and inorganic halide.

The precursor $R^1R^2R^3SiORX$ was prepared in a hydrocarbon solution from the corresponding $\omega$-halo alkane-1-ol, typically containing 2 to 8 carbon atoms, and a $R^1R^2R^3SiX$ compound wherein $R^1R^2R^3$ have the meanings ascribed above, for example tertiarybutyldimethylsilyl chloride, and imidazole. The reaction is conducted at temperatures between zero and 100° C. but preferably between room temperature and about 60° C. At the end of the reaction, the insoluble imidazole hydrohalide was removed by filtration, and the filtrate concentrated to afford essentially pure product $R^1R^2R^3SiORX$. The $R^1R^2R^3SiORX$ product was then reacted with lithium metal to form the $R^1R^2R^3SiORLi$.

The following examples further illustrate the invention.

1. Preparation of 3-(t-Butyldimethylsilyloxy)-1-Propyllithium at 60° C. (8613)

A one liter, three-necked, Morton flask was fitted with a mechanical stirrer, a 250 ml pressure-equalizing addition funnel, and a Claisen adapter equipped with a thermocouple, a reflux condenser, and an argon inlet. This apparatus was dried in an oven overnight at 125° C., assembled hot, and allowed to cool to room temperature in a stream of argon. Lithium metal dispersion, lot 8458, 0.80% sodium, was washed free of mineral oil with hexane (2×100 ml), and pentane (1×100 ml). The resultant lithium dispersion was dried in a stream of argon, weighed (11.70 grams, 1.686 mole, 2.80 equivalents), and transferred to the reaction flask with 500 ml cyclohexane. The reaction mixture was stirred at 450 RPMs, and heated to 65° C. with a heating mantle. The heat source was removed. 3-(t-Butyldimethylsilyloxy)-1-chloropropane, 139.56 grams of 90% assay, 0.602 mole, 1.00 equivalent, was added dropwise via the additional funnel. An exotherm was detected after 12% of the feed has been added. A dry ice/hexane cooling bath was applied as needed to maintain the reaction temperature between 60°-65° C. The total feed time was 112 minutes. The cooling bath was removed at the end of the halide feed. The reaction temperature fell off rapidly to room temperature. The reaction mixture was stirred for one hour at 450 RPMs, and one hour at 300 RPMs. The reaction mixture was transferred with argon pressure to a dry pressure filter, which contained a bed of filter aid. The product solution was pressure filtered with 3 psi (20.68×10$^3$ Pa) argon. The lithium chloride muds were reslurried with fresh cyclohexane (2×75 ml.). The filtrate was a clear, orange solution, yield=750 ml., 591.7 grams.

Total Base=17.7 wt. %.
Active C—Li=17.1 wt. %.
Yield=93.3% (based on active analysis).
Chloride=55 ppm.

This example was repeated a number of times employing the same or different (t-butyldimethylsiloxy)-1-chloroalkanes and different reaction temperatures. The products produced, and reaction conditions are listed in the Table. The products in the Table are as follows: {1}6-(t-butyldimethylsilyloxy)-1-hexyllithium; {2}3-(t-butyldimethylsilyloxy)-2,2-dimethyl-1-propyllithium; {3}3-(t-butyldimethylsilyloxy)-1-propyllithium, and {4}4-(t-butyldimethylsilyloxy)-1-butyllithium.

COMPARATIVE EXAMPLE

Preparation of 3-(t-Butyldimethylsilyloxy)-1-Propyllithium at 40° C. (8614)

A one liter, three-necked, Morton flask was fitted with a mechanical stirrer, a 250 ml pressure-equalizing addition funnel, and a Claisen adapter equipped with a thermocouple, a reflux condenser, and an argon inlet. This apparatus was dried in an oven overnight at 125° C., assembled hot, and allowed to cool to room temperature in a stream of argon. Lithium metal dispersion, lot 8458, 0.80% sodium, was washed free of mineral oil with hexane (2×100 ml), and pentane (1×100 ml). The resultant lithium dispersion was dried in a stream of argon, weighed (10.40 grams, 1.498 mole, 2.80 equivalents), and transferred to the reaction flask with 450 ml cyclohexane. The reaction mixture was stirred at 450 RPMs, and heated to 45° C. with a heat gun. 3-(t-Butyldimethylsilyloxy)-1-chloropropane, 124.02 grams of 90% assay, 0.535 mole, 1.00 equivalent, was added dropwise via the addition funnel. No exotherm was noted after 24% of the feed had been added. Therefore, the feed was halted. An exotherm was observed after a further 20 minutes of stirring. The feed was resumed after the exotherm had subsided. A dry ice/hexane cooling bath was applied as required to maintain the reaction temperature at 40°-45° C. The total feed time was 127 minutes. At the end of the feed, the cooling bath was removed. The reaction continued to exotherm for another hour after the end of the feed. The reaction mixture was stirred for one hour at 450 RPMs, and let stir overnight at 300 RPMs, under a blanket of argon. In the morning, the reaction mixture was transferred with argon pressure to a dry pressure filter, which contained dry filter aid. The product solution was pressure filtered with 3 psi (20.68×10 Pa) argon. This afforded a clear, dark yellow solution, yield=660 ml, 534.10 grams.

Total Base=13.9 wt. %
Active C—Li=13.1 wt. %.
Yield=72.6% (based on active analysis).
Chloride=431 ppm.

PREPARATION OF THE STARTING MATERIAL

3-(t-Butyldimethylsilyloxy)-1-Chloropropane (8424)

A 2 liter, three-necked flask was fitted with a mechanical stirrer, a 250 ml pressure-equalizing addition funnel, and a Claisen adapter equipped with a reflux condenser, a thermocouple and an argon inlet. This apparatus was dried in an oven overnight at 125° C., assembled hot, and allowed to cool to room temperature in a stream of argon. The flask was then charged with t-butyldimethylsilyl chloride, 221.00 gram (1.466 moles, 1.01 equivalents), imidazole, 101.80 grams (1.495 moles, 1.03 equivalents), and cyclohexane, 850 grams. The t-butyldimethylsilyl chloride dissolved rapidly in the reaction medium, endothermically. The imidazole remained insoluble. 3-Chloro-1-propanol, 137.27 grams (1.452 moles, 1.00 equivalent) was then added dropwise via the addition funnel. The reaction temperature climbed 22° C. during the course of the chloroalcohol addition. The total feed time was 75 minutes. The addition funnel was rinsed with additional cyclohexane, 50 grams. After the exotherm subsided (about one hour), the reaction mixture was heated to 40° C. with a heating mantle controlled by a Thermo-Watch. A fluffy white precipitate formed during the reaction. Periodically, the stirrer was halted, and the clear, supernatant solution was analyzed by gas chromatography (GC). After four hours at 40° C., all the starting material had been consumed, with the formation of a single, higher boiling compound. The reaction mixture was stirred overnight at 40° C., let cool to room temperature, then transferred to a medium porosity glass filter funnel. The flask was rinsed with fresh cyclohexane (2×250 ml). The filter cake was reslurried with cyclohexane (2×350 ml). The combined filtrate was concentrated on the rotary evaporator, bath temperature=30° C. This afforded a clear, colorless oil, yield=296.1 grams (97.7%). GC assay: Product 95.8%, cyclohexane 3.15%, 3-chloro-1-propanol 0.05% and unknowns 1.42%.

TABLE

| PRODUCT | LOT | SCALE | % XS LI | TEMP | WT % | YIELD | CL (ppm) |
|---|---|---|---|---|---|---|---|
| 1 | 8267 | 500 ml | 20 | 40–45 | 12.5 | 77.5 | |
| 1 | 8274 | 500 ml | 20 | 40–45 | 14.2 | 85.8 | |
| 1 | 8373 | 1 l | 40 | 60–65 | 14.9 | 89.8 | 38 |
| 1 | 8389 | 5 l | 40 | 60–65 | 12.5 | 90.1 | 27 |
| 1 | 8402 | 5 l | 60 | 60–65 | 12.5 | 89.3 | <20 |
| 1 | 8423 | 1 l | 40 | 60–65 | 14.9 | 88.9 | 41 |
| 2 | 8317 | 500 ml | 20 | 55–60 | 11.3 | 74.2 | |
| 2 | 8318 | 500 ml | 20 | 55–60 | 9.4 | 68.4 | |
| 2 | 8408 | 1 l | 40 | 60–65 | 14.1 | 88.8 | 54 |
| 2 | 8426 | 5 l | 40 | 60–65 | 14.3 | 89.1 | 20 |
| 3 | 8449 | 1 l | 40 | 60–65 | 15.0 | 91.0 | 23 |
| 3 | 8450 | 1 l | 50 | 60–65 | 14.2 | 90.0 | 16 |
| 3 | 8458 | 5 l | 50 | 60–65 | 13.8 | 90.6 | 36 |
| 3 | 8489 | 5 l | 40 | 60–65 | 16.8 | 92.3 | 68 |
| 3 | 8495 | 5 l | 40 | 60–65 | 15.0 | 90.3 | 41 |
| 3 | 8497 | 5 l | 40 | 60–65 | 15.7 | 95.1 | 25 |
| 3 | 8602 | 1 l | 40 | 80 Reflux | 14.3 | 84.9 | 208 |
| 3 | 8603 | 1 l | 40 | 80 Reflux | 14.9 | 79.7 | 316 |
| 3 | 8613 | 1 l | 40 | 60–65 | 17.1 | 93.3 | 55 |
| 3 | 8614 | 1 l | 40 | 40–45 | 13.1 | 72.6 | 431 |
| 3 | 8626 | 1 l | 40 | 40–45 | 10.3 | 57.0 | 1400 |
| 4 | 8561 | 1 l | 40 | 60–65 | 12.5 | 74.8 | |

What is claimed is:

1. A process for preparing functionalized alkyllithium compounds comprising reacting a fine particle size lithium metal of not more than 300 microns average particle size with an organosiloxyalkyl halide of the formula $R^1R^2R^3SiORX$ wherein $R^1$, $R^2$ and $R^3$ are independently selected from alkyl groups containing 1 to 10 carbon atoms and aryl groups containing 6 to 10 carbon atoms, R is selected from alkyl groups containing 2 to 8 carbon atoms either straight chain or substituted by alkyl or aryl groups, X is selected from chlorine or bromine, the reaction temperature is above 50° C., the reaction medium is a hydrocarbon solvent and the reaction is conducted in an inert atmosphere.

2. The process of claim 1 where in the organosiloxyhalide is selected from 6-(t-butyldimethylsilyloxy)-1-hexylhalide, 3-(t-butyldimethylsilyloxy)-2,2-dimethyl-1-propylhalide, 3-(t-butyldimethylsilyloxy)-1-propylhalide, 4-(t-butyldimethylsilyloxy)-1-butylhalide, 3-(t-butyldimethylsilyloxy)-2-methyl-1-propylhalide 8-(t-butyldimethylsilyloxy)-1-octylhalide, 6-(triisopropylsilyloxy)-1-hexylhalide, 3-(triisopropylsilyloxy)-2,2-dimethyl-1-propylhalide; 3-(triisopropylsilyloxy)-1-propylhalide, 4-(triisopropylsilyloxy)-1-butylhalide, 3-(triisopropylsilyloxy)-2-methyl-1-propylhalide, 8-(triisopropylsilyloxy)-1-octylhalide, 6-(t-butyldiphenylsilyloxy)-1-hexylhalide, 3-(t-butyldiphenylsilyloxy)-2,2-dimethyl-1-propylhalide, 3-(t-butyldiphenylsilyloxy)-1-propylhalide, 4-(t-butyldiphenylsilyloxy)-1-butylhalide, 3-(t-butyldiphenylsilyloxy)-2-methyl-1-propylhalide and 8-(t-butyldiphenylsilyloxy)-1-octylhalide.

3. The process of claim 2 wherein the halide is selected from chloride and bromide.

4. The process of claim 1 wherein the reaction temperature is between 50° C. and 160° C.

5. The process of claim 1 wherein the lithium metal is used in an excess amount of 1 to 100% excess over the stochiometric amount.

6. The process of claim 1 wherein the fine particle size lithium metal has a particle size range of 10 to 300 microns.

7. The process of claim 6 wherein the fine particle six lithium has a sodium content of 0.40 to 0.76 weight percent.

8. A process for preparing functionalized alkyllithium compounds comprising reacting a fine particle size lithium metal of not more than 300 microns average particle size with an organosiloxyalkyl halide selected from 6-(t-butyldimethylsilyloxy)-1-hexylhalide, 3-(t-butyldimethyl-silyloxy)-2,2-dimethyl-1-propylhalide, 3-(t-butyldimethylsilyloxy)-1-propylhalide, 4-(t-butyldimethylsilyloxy)-1-butylhalide, 3-(t-butyldimethyl-silyloxy)-2-methyl-1-propylhalide 8-(t-butyldimethylsilyloxy)-1-octylhalide, 6-(triisopropylsilyloxy)-1-hexylhalide, 3-(triisopropylsilyloxy)-2,2-dimethyl-1-propylhalide; 3-(triisopropylsilyloxy)-1-propylhalide, 4-(triisopropylsilyloxy)-1-butylhalide, 3-(triisopropylsilyloxy)-2-methyl-1-propylhalide, 8-(triisopropylsilyloxy)-1-octylhalide, 6-(t-butyldiphenylsilyloxy)-1-hexylhalide, 3-(t-butyldiphenylsilyloxy)-2,2-dimethyl-1-propylhalide, 3-(t-butyldiphenylsilyloxy)-1-propylhalide, 4-(t-butyldiphenylsilyloxy)-1-butylhalide, 3-(t-butyldiphenylsilyloxy)-2-methyl-1-propylhalide and 8-(t-butyldiphenylsilyloxy)-1-octylhalide, the halide is selected from chlorine or bromine, the reaction temperature is above 50° C., the reaction medium is a hydrocarbon solvent and the reaction is conducted in an inert atmosphere.

9. The process of claim 8 wherein the reaction temperature is between 50° C. and 160° C.

10. The process of claim 8 wherein the lithium metal is used in an excess amount of 1 to 100% excess over the stochiometric amount.

11. The process of claim 8 wherein the fine particle size lithium metal has a particle size range of 10 to 300 microns.

12. The process of claim 11 wherein the fine particle six lithium has a sodium content of 0.40 to 0.76 weight percent.

13. The process of claim 1 wherein the organosiloxyalkyl halide of the formula $R^1R^2R^3SiORX$ is prepared in a hydrocarbon solvent by reacting an ω-halo alkane-1-ol, containing 2 to 8 carbon atoms, with a compound of the formula $R^1R^2R^3SiX$ wherein $R^1$, $R^2$ and $R^3$ are independently selected from alkyl groups containing 2 to 10 carbon atoms and aryl groups containing 6 to 10 carbon atoms, R is selected from alkyl groups containing 1 to 8 carbon atoms either straight chain or substituted by alkyl or aryl groups, X is selected from chlorine or bromine and imidazole at a temperature between zero and 100° C.

* * * * *